United States Patent
Günzler et al.

(10) Patent No.: US 7,260,179 B2
(45) Date of Patent: Aug. 21, 2007

(54) METHOD FOR PRODUCING X-RAY IMAGES

(75) Inventors: Florian Günzler, Nürnberg (DE);
Martin Spahn, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/410,468

(22) Filed: Apr. 25, 2006

(65) Prior Publication Data

US 2006/0245545 A1 Nov. 2, 2006

(30) Foreign Application Priority Data

Apr. 29, 2005 (DE) .................. 10 2005 020 505

(51) Int. Cl.
*H05G 1/64* (2006.01)
(52) U.S. Cl. .................. 378/98.4; 378/98.11
(58) Field of Classification Search ............ 378/98.12, 378/98.9, 98.11, 62, 9, 87
See application file for complete search history.

(56) References Cited

U.S. PATENT DOCUMENTS 6,980,626 B2 * 12/2005 Groh et al. .................. 378/87

OTHER PUBLICATIONS

M. Spahn, V. Heer and R. Freytag, "Flachbilddetektoren in der Röntgendiagnostik", Radiologe 2003, pp. 340-350.
Erich Krestel, "Imaging Systems for Medical Diagnostics", Siemens Aktiengesellschaft, Berlin and Munich, Germany, 1990, pp. 408-415.

* cited by examiner

*Primary Examiner*—Hoon Song

(57) ABSTRACT

The invention relates to a method for producing X-ray images, by which successive X-ray images are recorded using a first semiconductor detector arranged in a first plane and a second semiconductor detector arranged in a second plane. For the purpose of correcting the X-ray images it is proposed that dark images are recorded intermittently, and these are subtracted from the X-ray images subsequently generated.

11 Claims, 2 Drawing Sheets

METHOD FOR PRODUCING X-RAY IMAGES

CROSS REFERENCE TO RELATED APPLICATIONS

This application claims priority to the German Application No. 10 2005 020 505.4, filed Apr. 29, 2005 which is incorporated by reference herein in its entirety.

FIELD OF INVENTION

The invention relates to a method for producing X-ray images.

BACKGROUND OF INVENTION

Such a method in accordance with the prior art is known, for example, from "Imaging Systems for Medical Diagnostics"; Editor: E. Krestel, 1990, Siemens Aktiengesellschaft, Berlin and Munich, pages 408 to 415.

SUMMARY OF INVENTION

With the known method, the problem arises that directional radiation through a body towards a first semiconductor detector produces scattered radiation which falls onto a second semiconductor detector. The same also applies in reverse, i.e. when radiation is directed towards the second semiconductor detector, scattered radiation reaches the first semiconductor detector. The undesired scattered radiation which is received results in inaccuracies in the X-ray images. In order to counteract this disadvantage, the procedure adopted in the prior art is to alternate the irradiation of the first and second semiconductor detectors with X-rays. However, doing this requires that whichever semiconductor is not currently active must wait until the signals generated by the preceding exposure have been read out. As a consequence, a relatively long time elapses between any two X-ray pulses directed towards the one and same semiconductor detector.

An object of the invention is to eliminate this disadvantage of the prior art. In particular, it is to specify a method for producing X-ray images which has an improved speed.

This object is achieved by the claims.

As stipulated by the invention, provision is made for the following method steps:

c1) Omission of at least one of the first X-ray pulses, so that the first semiconductor detector records only a first dark image, produced by scattered radiation, c2) Omission of at least one of the second X-ray pulses, so that the second semiconductor detector records only a second dark image, produced by scattered radiation, d) Storage of the first and second dark images, e1) Correction of the first X-ray images, subsequently recorded by the first semiconductor detector, by using the first dark image, and e2) Correction of the second X-ray images, subsequently recorded by the second semiconductor detector, by using the second dark image.

With the proposed method steps, it is possible to achieve a substantially improved speed for the generation of X-ray images. In particular, it is no longer necessary always to switch off one of the two semiconductor detectors during the recording time of the other semiconductor detector. It is no longer necessary for the purpose of producing X-ray images for the X-ray pulses to be generated with a time offset. In particular it is conceivable that, if the X-ray pulses are generated simultaneously, only one X-ray source is used for generating the X-ray pulses.

In accordance with an advantageous form of embodiment, a first X-ray source which is arranged opposite the first semiconductor detector is provided for generating the first X-ray pulses, and a second X-ray source which is arranged opposite the second semi conductor detector for generating the second X-ray pulses. The first and second X-ray sources can be independently induced to generate the first and second X-ray pulses. This enables the parameters of the method to be simply adjusted for the applicable conditions. In particular, any time offset of the first and second X-ray pulses can be varied.

In accordance with another form of embodiment provision is made, for correction purposes, for subtracting the first dark image from each of the first X-ray images subsequently recorded, and the second dark image from each of the second X-ray images subsequently recorded. This is a correction which is simple and quick to perform. It is expedient to apply it to at least two of the first or second X-ray images which are subsequently recorded.

In accordance with a further form of embodiment, the steps labeled c1) to e2) are repeated after a prescribed number of X-ray pulses, and the previously recorded first dark image or second dark image is replaced respectively by another first or second dark image. The proposed correction can thereby be continuously updated and if necessary adjusted for changes in the scattering conditions.

Repetition of the steps labeled c1) to e2) can, in particular, be initiated by a signal supplied by a movement detection device for detecting movement of the patient. In particular, if the position of the patient changes relative to the position of the semiconductor detectors, it is to be expected that the scattered radiation will change. In such a case, the proposed movement detection device enables an appropriately modified correction to be applied immediately, using the method in accordance with the invention.

In accordance with a further form of embodiment, the first and second X-ray pulses are generated with a time offset or simultaneously. In particular, a further improvement in the speed with which X-ray images are produced can be achieved by the overlapped or simultaneous generation of the X-ray pulses.

It is expedient if the first and second X-ray pulses are generated with the same pulse width. This permits simple synchronization of the signals recorded by the first and second semiconductor detectors and the X-ray images reconstructed from them.

Provision is made in accordance with a further form of embodiment that the semiconductor detector is read out and then reset to an initial state in a ti me gap between the X-ray pulses. It is, in particular, no longer necessary to provide an additional waiting time during the time gap, during which the other semiconductor detector is exposed to X-rays. The semiconductor detector can thus be reset to an initial state immediately after the read-out, and is then immediately ready again to record signals.

Provision is made in accordance with a further form of embodiment that during the recording of a dark image either the X-ray image recorded immediately beforehand, or an image generated by means of extrapolation using a prescribed algorithm, is displayed. For the viewer this means that no gaps appear in the generation of images. It avoids an unwanted flickering on the display device caused by the lack of display of the X-ray image which is not generated during the recording of a dark image.

On current X-ray equipment which is designed for operation using two semiconductor detectors arranged in different planes, the so-called biplanar mode, the proposed method can be performed without any changes to the hardware. For the purpose of performing the method in accordance with the invention, it is only necessary to amend or replace any software used for controlling such equipment.

BRIEF DESCRIPTION OF THE DRAWINGS

An exemplary embodiment of the invention is explained below in more detail by reference to the drawings. These show.

DETAILED DESCRIPTION OF INVENTION

Figure 1:
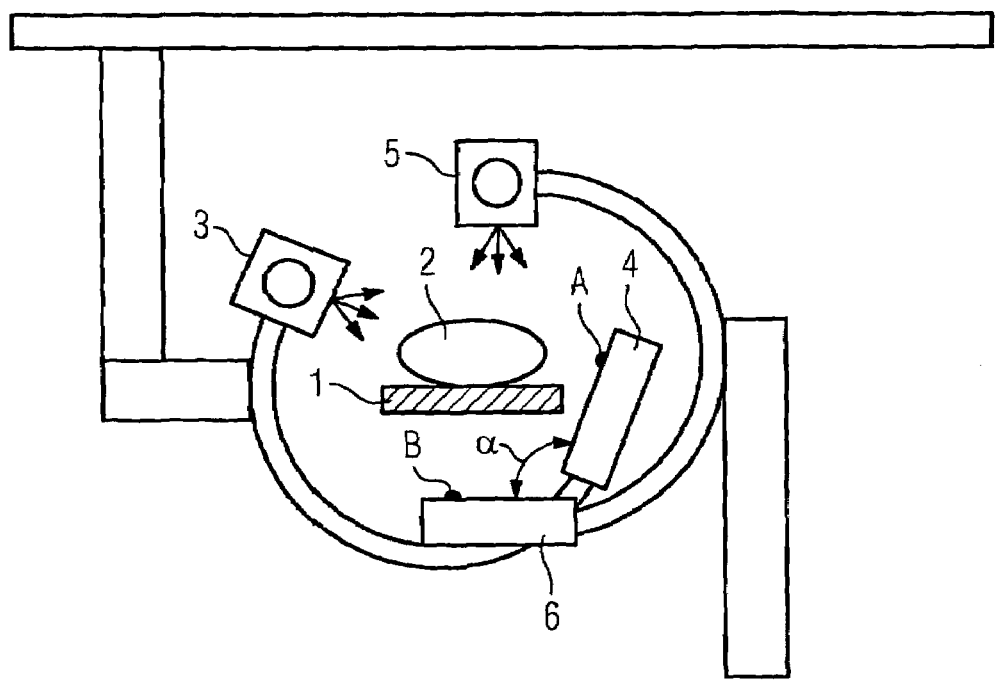
FIG. 1 a schematic sectional view of a state-of-the-art X-ray device with two semiconductor detectors, FIG. 2 a partly cut-away perspective view of a state-of-the-art semiconductor detector, FIG. 3 schematic of a mode of operation for producing X-ray recordings in accordance with the prior art, and FIG. 4 schematic of the mode of operation for producing X-ray images in accordance with the invention.

FIG. 1 shows a schematic sectional view of a state-of-the-art X-ray device. A body 2 which is to be X-rayed is held on a bed 1. Arranged opposite a first X-ray source 3 is a first semiconductor detector 4, and opposite a second X-ray source 5 is a second semiconductor detector 6. A first plane A, which lies parallel to a detector surface on the first semiconductor detector 4, cuts a second plane B, which lies parallel to a detector surface on the second semiconductor detector 6, at an angle α, which is preferably greater than 80 degrees and less than 150 degrees.

Figure 2:
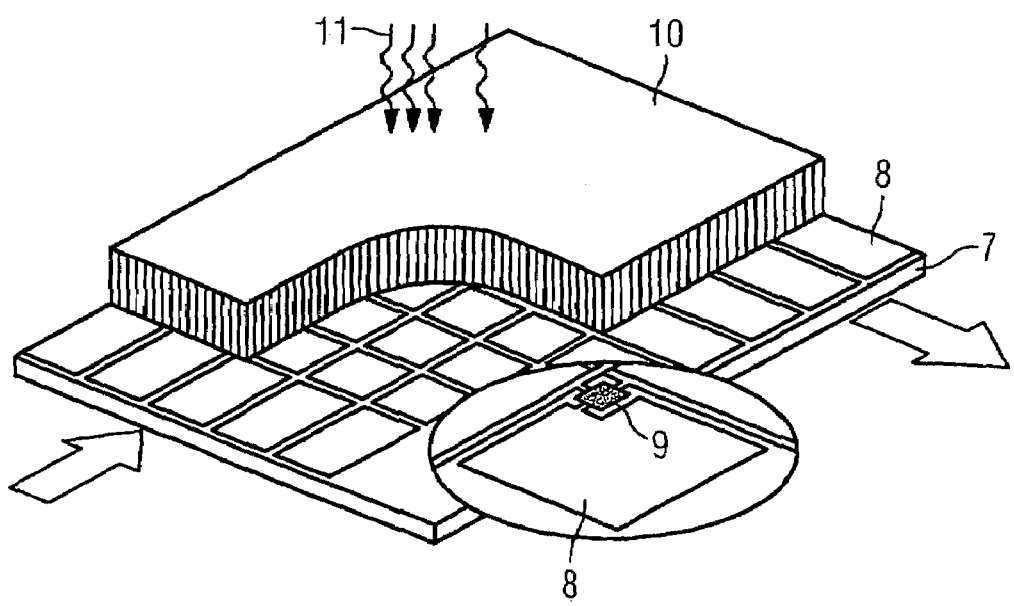

FIG. 2 shows a partly cut-away perspective view of a state-of-the-art semiconductor detector. The example shown is a semiconductor detector in which a multiplicity of photodiodes 8 are arranged, in the nature of a matrix, on a substrate 7. Each of the photodiodes 8 can have a switch 9, with which the photodiodes 8 can be switched to record a signal or to read out. The photodiodes 8 are overlaid with a converter layer 10 which converts X-rays 11 into visible light. It is expedient if the converter layer 10 is manufactured from a scintillating material, for example CsI or something similar. Apart from the semiconductor detectors shown in FIG. 2, it would however also be possible within the ambit of the invention to use semiconductor detectors which are otherwise constructed, in particular including direct-conversion semiconductor detectors, with which X-ray quanta are converted directly to charges. In relation to the construction and method of working of suitable semiconductor detectors, refer to the publication "Spahn et. al., Flachbilddetektoren in der Röntgendiagnostik [Flat panel image detectors in X-ray diagnostics], Radiologe 43 (2003) pages 340 to 350". The disclosure content of this document is herewith incorporated.

Figure 3:
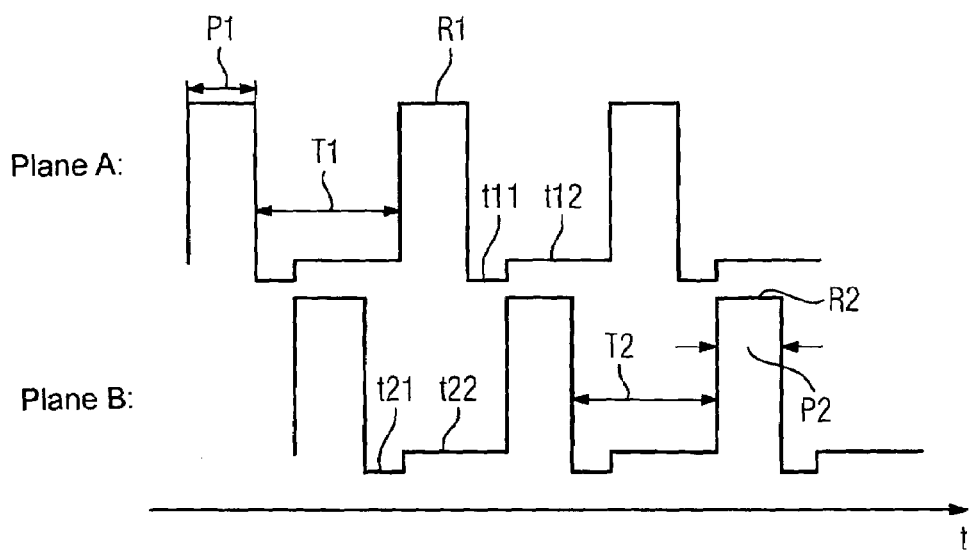

FIG. 3 shows in schematic form a mode of operation in accordance with the prior art. Against time t is plotted in schematic form and in arbitrary units a signal level which can be measured by means of the semiconductor detectors 4, 6. As can be seen from FIG. 3, the first X-ray source 3 and the second X-ray source 5 can be so controlled that they generate first X-ray signals R1 and second X-ray signals R2 with an equal signal width P1, P2. A time interval T1, T2 which is located between two successive X-ray signals R1, R2 is made up of a first time sub-interval t11, t21, during which the semiconductor detectors 4, 6 are read out and a second time sub-interval t12, t22, during which the semiconductor detectors 4, 6 are either inactive or are reset by connecting the photodiodes 8 to ground, as appropriate.

For the X-ray pulses which generate the X-ray signals R1, R2, the duty time is chosen such that in each case the semiconductor detector 4, 6 associated with the other X-ray source, 3, 5 respectively, is inactive, i.e. the duty time is in the second time sub-interval t12, t22. The second time sub-interval t12,t22 is in each case chosen such that it is longer than the pulse signal P1, P2.

Figure 4:
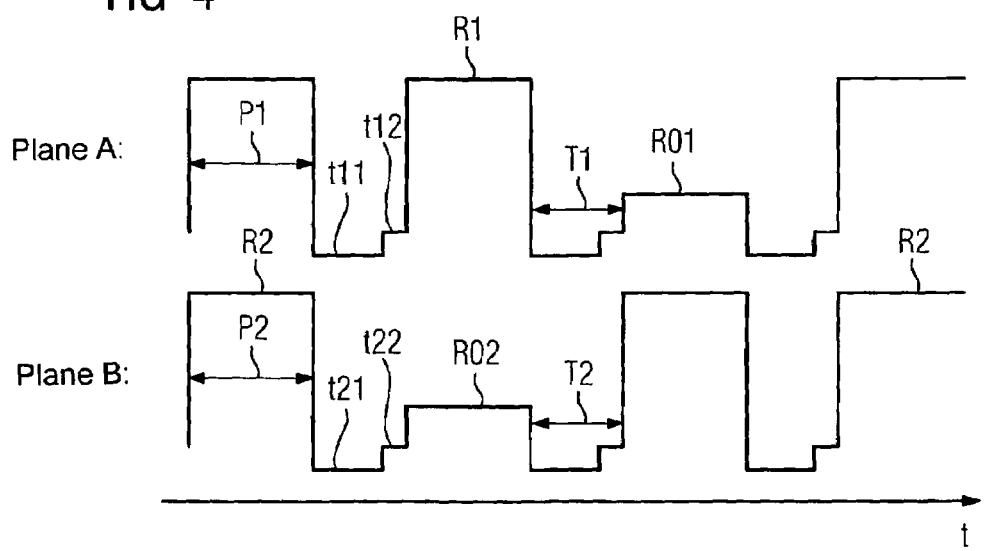

FIG. 4 shows the method in accordance with the invention in a diagram which is comparable with. FIG. 3. Here too, X-ray signals R1, R2 with equal signal width P1, P2 are generated by the X-ray sources 3, 5. In the case shown, the X-ray signals R1, R2 are generated simultaneously. However, it is also possible for the X-ray signals R1, R2 to be generated with a time offset so that they overlap or are each generated, like those in FIG. 3, exactly when the other X-ray source 3, 5 is inactive.

In accordance with the invention, an X-ray pulse is omitted at a prescribed time both from the sequence of first X-ray pulses, generated by the first X-ray source 3, which generate the first X-ray signals R1 and also from the sequence of second X-ray pulses, generated by the second X-ray source 5, which generate the second X-ray signals R2. In this case, the corresponding semiconductor detector 4, 6 detects only the scattered radiation which forms as a consequence of the X-ray pulse generated by the other X-ray source 3, 5 in conjunction with the body 2. In this case, the semiconductor detector 4, 6 which is opposite the inactive X-ray source 3, 5 measures a scattered radiation signal R01, R02. The scattered radiation signal R01, R02 corresponds to a dark image. It is stored by means of a computer, and for correction purposes is subtracted from the X-ray signals R1, R2 measured subsequently using the semiconductor detectors 4, 6.

The X-ray pulses can be omitted in prescribed time intervals. However, and possibly additionally, a movement detector can be provided to detect movements of the body 2. The movement detector can trigger a signal, which in turn initiates the omission of an X-ray pulse and the simultaneous recording of a dark image.

The invention claimed is:

1. A method of generating X-ray images for a medical procedure using at least one X-ray source, a first semiconductor detector arranged in a first plane and second semiconductor detector arranged in a second plane different from the first plane, the method comprising:
generating a sequence of first X-ray pulses for recording a sequence of first X-ray images using the first semiconductor detector;
generating a sequence of second X-ray pulses for recording a sequence of second X-ray images using the second semiconductor detector;
omitting at least one of the first X-ray pulses so that the first semiconductor detector records a first dark image caused by scattered radiation;
storing the first dark image;
recording the sequence of first X-ray images;
omitting at least one of the second X-ray pulses so that the second semiconductor detector records a second dark image caused by scattered radiation;
storing the second dark image;
recording the sequence of second X-ray images;
correcting the sequence of first X-ray images based on the first dark image;

correcting the sequence of second X-ray images based on the second dark image; and displaying the corrected sequence of first and second X-ray images and a first and second interim X-ray image while recording the first and the second dark images for performing the medical procedure.

2. The method in accordance with claim 1, wherein the X-ray source includes a first X-ray source arranged opposite the first semiconductor detector for generating the sequence of first X-ray pulses and a second X-ray source arranged opposite the second semiconductor detector for generating the sequence of second X-ray pulses.

3. The method in accordance with claim 1, wherein correcting the sequences of first and second X-ray images includes subtracting each of the first X-ray images with the first dark image and subtracting each of the second X-ray images with the second X-ray image.

4. The method in accordance with claim 1, wherein at least a further one of the first and second X-ray pulses is omitted after a prescribed number of first and second X-ray pulses has been emitted for generating updated first and second dark images.

5. The method in accordance with claim 4, wherein the omission of the at least a further one of the first respectively second X-ray pulses is triggered by a motion detection signal, the motion detection signal indicating a movement of a patient under X-ray examination.

6. The method in accordance with claim 1, wherein the sequences of first and second X-ray pulses are generated simultaneously.

7. The method in accordance with claim 1, wherein the sequence of second X-ray pulses has a time offset relative to the sequence of first X-ray pulses.

8. The method in accordance with claim 1, wherein the sequences of first and second X-ray pulses have an identical pulse width.

9. The method in accordance with claim 1, wherein the first and second semiconductor detectors are reset to an initial state after reading out the first and second semiconductor detectors, the reset executed in a time gap respectively between two first X-ray pulses and two second X-ray pulses.

10. The method in accordance with claim 1, wherein the first and second interim images are selected from the sequences of first and second X-ray images immediately recorded before recording the first and second dark images.

11. The method in accordance with claim 1, wherein the first and second interim images are extrapolated from at least one of the previously recorded first and second X-ray images.

* * * * *